United States Patent [19]

Smallbone

[11] Patent Number: 5,272,745
[45] Date of Patent: Dec. 21, 1993

[54] APPARATUS FOR ANALYZING, CONTINUOUSLY FLOWING DRY POWDER SAMPLES, BY MEANS OF X-RAY SPECTROSCOPY

[75] Inventor: Allan H. Smallbone, La Crescenta, Calif.

[73] Assignee: A.H.S. Consultants & Engineers, Inc., La Crescenta, Calif.

[21] Appl. No.: 882,871

[22] Filed: May 14, 1992

[51] Int. Cl.$^5$ ........................................... G01N 23/223
[52] U.S. Cl. ....................................... 378/47; 378/45; 250/255
[58] Field of Search .................. 378/44, 45, 51, 53, 378/54, 83, 46; 250/255, 306

[56] References Cited

U.S. PATENT DOCUMENTS

| | | | |
|---|---|---|---|
| 4,134,012 | 1/1979 | Smallbone et al. | 378/47 |
| 4,388,530 | 6/1983 | Lubecki et al. | 378/45 |
| 5,020,084 | 5/1991 | Robertson | 378/46 |
| 5,065,416 | 11/1991 | Laurila et al. | 378/53 |
| 5,107,527 | 4/1992 | Sipila et al. | 378/46 |

*Primary Examiner*—David P. Porta
*Assistant Examiner*—Kim-Kwok Chu

[57] ABSTRACT

This invention relates to the application of on-line or inprocess elemental analysis by X-ray fluorescence spectroscopy and in particular to improvements in the field of continuously analyzing flowing dry powder samples from processes such as raw mix cement, iron ore, slag, mineral concentrates, concentrator feeds, phosphate, food products and similar materials.

3 Claims, 8 Drawing Sheets

APPARATUS FOR ANALYZING, CONTINUOUSLY FLOWING DRY POWDER SAMPLES, BY MEANS OF X-RAY SPECTROSCOPY

DESCRIPTION OF THE PRIOR ART

To extract the desired minerals efficiently from an ore, or to effectively produce an optimum product from a mixture of minerals, a rapid on-line or in-product assay of the elements composing the minerals involved, is essential. Standard laboratory assays, while accurate, are expensive, time consuming and are rarely related to production in real time. The small quantity of sample normally extracted for such assays, from the immense volumes usually encountered in such production, is generally not well related to the information needed for accurate control. For example, assaying one ounce of the product a day, with the results being only available to the process personnel the following day, may not be at all indicative of the exact nature of the 30,000 tons that passed through the concentrator in that same day, the time delay effectively makes control extremely difficult.

With such a need for timely and relatively accurate assays being critical to the vast majority of processes, on-stream analysis is now accepted as a necessity in slurried and liquid based products.

However, efforts to assay flowing powders have not yet met the needs of most industries.

Current on-line slurry analytical systems have proved most effective in providing rapid information about the product at a relatively low cost thereby producing an economically efficient product.

Attempts to improve the accuracy of on-line methods of analysis and minimize errors such as density variations and inter-element effects have been undertaken by using either variations in the secondary X-ray beams or energy emitted from various wavelengths of background and then manipulating these data, or by using various mechanical means to enable samples of a process to be rapidly presented to the X-ray beam for analysis.

Anderman and Kemp, in U.S. Pat. No. 2,897,367 in 1959 described a system of detecting two different wavelengths of secondary X-ray Beams emanating from the same primary X-ray source and measuring the ratio of one beam to another. Corrections to the elemental assays for variations in sample position, variations in X-ray power and also the particle sizes of the ore containing the mineral were obtainable by using this method.

Furbee and Bernstein, in U.S. Pat. No. 3,150,261, in 1964 employed background radiation data to compensate for variations in slurry density.

Smallbone, in U.S. Pat. No. 3,388,427 dated 1968, designed an automatic briquette making machine to duplicate laboratory methods of preparing raw mix cement and similar dry materials for X-ray analysis.

Carr-Brion et al, in U.S. Pat. No. 3,443,092 dated 1969, designed a system to analyze the solid component of a slurry.

Rhodes, in U.S. Pat. No. 3,448,264 dated 1969, employed a method of measuring backscatter radiation from samples to correct the analysis.

Smallbone, in U.S. Pat. No. 3,742,226 dated 1973, Designed an automatically agitated X-ray fluorescence analysis cell to maintain solids in constant suspension during the analysis period of a liquid based slurry sample.

Carr-Brion and Bramwell, in U.S. Pat. No. 3,749,910, also employed background radiation to measure the particle size of the ore particles in a slurry.

Pick, in U.S. Pat. No. 3,752,979 dated 1973, employed a means of separating a stream of slurry into two separate components and compared the data from each to improve the accuracy of the analysis.

Tanguy, in U.S. Pat. No. 3,922,542 dated 1975, employed a device to continuously feed and sequentially analyze previously prepared briquette shaped samples.

Smallbone and Gurvich in U.S. Pat. No. 4,134,012, in 1979 employed a primary X-ray beam having two widely different wavelength areas of analysis and were able to obtain on-line analytical data of lighter elements such as Calcium in a heavy metallic ore slurry and also data relating to slurry density and particle size, thus enabling greater accuracy to be obtained for all elements of interest.

Lipshutz and Stark in U.S. Pat. No. 4,278,887 dated 1981 designed a sample flow cell with inlet and outlet ports for assaying fluid samples. The cell having a transparent window and a diffuse mirror to transmit radiation through the cell to achieve accurate spectrographic measurements.

In the case of dry powders, progress in automated on-line assay has not evolved as fast as it has in slurry applications. Generally, powders are much more difficult to maintain in a suitable position or perimeter, and once in position are not always amenable to reverting to free flow when required. Powders are reluctant to flow due to changes in humidity, increased surface tension, etc. and leftover particles from previous samples can, in some designs, create inter-sample contamination problems.

In most X-ray laboratory procedures for sample analysis, powder samples are finely ground in a manually controlled off-line grinding mill, to approximately 350 mesh, then mixed with a binding agent such as boric acid or pure cellulose powder and by using a high pressure press and dies, convert the sample into a hard, cohesive briquette to prevent its subsequent disintegration during handling and analysis. Great care must be exercised in always grinding sample to precisely the same size of particle and to apply a consistent even pressure in manufacturing the briquette to avoid serious errors in elemental analysis. Adding binder to a sample not only creates a considerable variation in the "sample to bulk" ratio and therefore to the resulting assay when incorrectly related to the bulk process, but even minor additions results in a loss of critical minor elemental intensity. Variations in sample briquetting pressure also introduces similar errors.

Other automated, but unpatented, attempts to copy laboratory dry powder sample handling standards by either automatically briquetting the powders or fusing dry samples at high temperature have been described in various publications, but they have experienced only small successes in the areas of on-line analysis and control.

Major problems when manually sampling either slurry or dry powder on-line assays, have been twofold.

Firstly, is the collected sample truly representative of the main product at that time? For example, occasional samples are frequently incorrectly extracted from the main product and may not be at all representative of the main product in elemental content, particle size or density.

Secondly, the other major error is caused by the inevitable incorrect or accidental dilution of the sample, either by liquid or dry binder additions. In most cases, liquid samples normally contain 30% to 50% water. For dry powders, the added binder is generally 50% boric acid or inert cellulose for soft coals to 75% boric acid for high silicate samples such as sand. This loss in intensity of low Z elements in the sample, or the unknown variations of critical low concentrations of elemental data due to errors in the dilution factor, can be most critical in obtaining accurate data relating to inter-element corrections and the percentage content of important elements that cause serious upsets in the production of certain minerals.

This invention takes advantage of the natural state of a main product by analyzing a continuous flow of a sample of dry powder in the 100% normal stage thus obtaining an important increase in the intensity of the secondary X-rays carrying elemental data to the X-ray detectors. These data contain the all-important minor and major elemental data necessary for interelement corrections as well as data relating to sample specific gravity, particle size and sample cell density (packing factor). For example, an increase of 50% to the lower elemental intensities can result in a dramatic improvement in data corrections.

These samples, retained within the "analyzing" cells, are analyzed in turn by one or more individual and different X-ray spectroscopic sources operating at specific and separate wavelengths, and having independent and distinct X-ray detector systems. Analytical data are obtained by measuring essentially the same area and depth of sample at these distinctly different wavelengths of X-ray fluorescence without the severe loss of intensity due to dilution factors and other sources of error. Essentially, samples are collected, retained and transported, within cells, in front of and in between one or more different systems of analysis. It is also appreciated that this movement, while currently preferred to be circular, it could readily be of a linear or elliptical motion. Analyzing samples continuously in an on-line, processional mode by one or more different X-ray analyzers readily produces data which is more meaningful to the main product or production method.

SUMMARY OF THE INVENTION

In the preferred mode of practicing this invention, a portion of a main product stream is continuously sampled to become an automated assay sample stream. The amount of sample extracted is directly related to the product and the desired speed of assays required for product control. For example, for some products, a minimum of 30 cubic inches, or approximately 2 to 3 lb. of sample is required every 60 seconds. However, the amount of sample extracted is not critical, either in quantity or frequency. Larger or smaller applications may require more or less sample and the size and volume of the cells may be varied to suit. The only requirement is that the sample in the cell be sufficient to be fully visible to the X-ray analyzer.

FIG. 1, shows a rotary application of the method of selecting, retaining, transporting and analyzing a sample and in this composite drawing shows the relationship of a feed sample unit, front elevation, at section 300—300 of (FIG. 2) to a front elevation, section 300—300, of the Analyzer Sample unit (FIG. 3).

FIG. 1A, similarly, is a composite drawing and shows the relationship of a side elevation at section 400—400 of the feed sample unit (FIG. 3) to a side elevation section 400—400 of the analyzer sample unit (FIG. 4).

The displayed separation of feed sample and analyzer sample units, in both FIGS. 1 and 1A, is non-critical and can be of any reasonable length, according to plant or product flow requirements. Generally, the feed sample unit should preferably be installed above the analyzer sample unit to take advantage of the free flow of powder by gravity. Otherwise, it will be necessary to use a small conveyor or other means to move the feed sample output into the input section of the analyzer sample unit.

A flowing stream of sample from the main product enters a cell of the feed unit at the top inlet "X" (146,) (FIG. 2.) The average amount, dependent on sample cell dimensions, ~30 cubic inches or more, of selected sample will fill a cell in the feed unit, (117,143,144,).

The "feed unit" consists of a central hub (117) having a desired number of spokes which form the two sides of each cell. A circular front plate (143) and a back circular plate (144) form the back and front plates of the cells and each part is firmly attached to each other and the main drive shaft (110) and rotates counter-clockwise with the main drive shaft as one unit. The top of each cell remains open to accept and deliver a quantity of sample.

Excess sample from the flowing stream will overflow each of the cells, as they are presented in turn for filling, and the excess will continue flowing down the outlet pipe on the left side to exit at (4), and rejoin the main product stream.

Connected to the feed sample unit by a suitably sized conduit for the transfer of the selected sample, the analyzer sample unit (FIG. 3) below the feed sample unit contains another similar unit (6,7,8,9.) The upper and lower cells (7,117) of the feed sample and analyzer sample units are also mechanically connected by roller chain and sprockets (13,16,113,116) or gears mounted on the main shafts (10,110) and rotate counter-clockwise in unison when requested by the controlling unit. The units may driven by either mechanical, pneumatic or hydraulic power applied to the lower shaft (10,12,26,27,29) or to each shaft (10,110) separately and turned in unison through a common electrical driver and circuit. Both main shafts of each unit are mounted on ball bearings (11,111.) Ball bearings are sealed from dust, moisture etc. by the bearing housing supports (30,130.) Mechanical supports for both feeder sample unit and the analyzer sample unit are shown as (2,3,15,114,140,141,142.) and are robustly connected by normal mechanical methods to provide positive stability. Dust is excluded from interfering with operating units by "O" ring seals (35,145.)

In the analyzer sample unit, (FIG. 3) the front and back rotating plates, forming the front and rear ends of the analysis cells (6,9) have apertures (36,31a respectively,) positioned in the lower center of each cell of both of the rotating end plates. Each cell front aperture and cell rear aperture is covered with a film that is transparent toward types of X-ray Fluorescence radiation used and which is appropriate for each particular sample of a production line or process system. Variable thicknesses of window may be used for various applications.

One or more separate and different X-ray analytical units (1,1a) are mounted over one or more of the stationary front plate apertures (34,34a). One is mounted on the stationary front plate, over the vertically uppermost cell (34) and the other, also mounted on the stationary front plate, at a position 45 degrees, anti-clockwise direction to the left, (34a). Positioned on the stationary back plate (15) of the device are separate detectors (32,33) mounted to accept X-rays passing through the front plate apertures, (36) passing through the sample (AS) in the cell, through the back plate apertures (31,28) and into the rear detector (32,33.)

In an operating mode, sample flows continually into point "X" of the upper feed sample unit. Sample deposited at point "X" falls into an open cell below. Movements of the units will now move a filled cell anti-clockwise from the loading position (FS FIG. 2) to "FS1" and then through "FS2" where a retaining plate (112) retains the sample in position in each cell during motion. To start the operation, both upper and lower are rotated in unison four times. In the feed sample unit, the sample has now moved from position "FS" on unit FIG. 1, through "FS1" to "FS2". On reaching position "FS3" loose sample falls from the cell and down chute (118) where slide valve (120,123) first closes and then opens with each subsequent movement of the upper unit allowing sample to fall successively into the analyzer sample unit cells "AS","AS1" and "AS2" of the lower analyzer sample unit. The slide valve (120,123) is timed to close before the system moves, then to open after motion has stopped, to control and then deliver a correct portion of sample from cell "FS3" into a cell "AS" of the analyzer unit and then to close again to prevent other sample from accidentally entering the cell.

After the initial four movements, when the apparatus is in control mode, if sample is available, there will always be sample in cells "FS" through "FS2", and "AS" through "AS1". At "AS2" and "AS3", analyzed sample will have fallen out of the analyzer cells into exit (4) and with the excess sample falling down the overflow (4) from the Feed unit (122,146), move together to rejoin the main product stream.

Following delivery of sample from the feed unit, the level of sample in cell "AS" (AS) is approximately "full". When the cell in the analyzer unit moves to position "AS1" the cell will still be "full" of sample, but the top level of sample in the cell may cant slightly, when tilted to a 45 degree position (AS1.) However, the lower level of the sample in "AS1" within sight of the transparent window (36), remains essentially as it was in the "AS" position, and exposes the identical initial area of sample to a different X-ray unit having a specific fluorescent beam and wavelength, and an independent detector system.

After samples have been assayed in turn by one or more X-ray systems, powder sample then exits the cells and successively falls into the return sample chute (4).

For some applications, such as low atomic number (Z) elements within a sample, the analytical areas of the plastic windows, may be flushed with helium gas to displace the normal air atmosphere through which primary and secondary X-rays will travel. This well-known procedure will further enhance the intensity of critical elemental data.

Empty sample cells that have retained and transported samples for analysis, are cleaned of any retained dust by pipes (37) blowing dry nitrogen into the cells. Any dust is excluded from the other areas by dust seals (38,39.)

Analysis of the samples is obtained by using standard X-ray tube spectroscopy techniques as depicted in FIG. 6 and by busing standard radioactive-isotope spectroscopy techniques as depicted in FIG. 7.

In FIG. 6, a typical X-ray tube having a tube body, filament and a target, (1,2,3) is used. Primary X-rays are emitted (4) passing through apertures and an X-ray transparent window in the cells (8,9,10) to enter the sample (11). Secondary X-rays (5) are emitted by elements within the sample and return to the X-ray detector (6) for processing. Primary X-rays (4) also penetrate the sample thickness and pass through another X-ray transparent window (14) and apertures (13,15) to enter a second X-ray detector (7) for processing. Lower closed section of the cell is shown as (12).

Similarly, in FIG. 7 a form of a radioactive-isotope spectroscopic system is used as an additional method of analysis. The radioactive source and holder (1,2) emits primary X-rays (4) which pass through apertures (8,9) and X-ray transparent window (10) to enter sample (11). Secondary X-rays (5) are emitted by elements within the sample and return to the X-ray detector (3) for processing. Primary X-rays (4) also penetrate the sample before passing through the X-ray transparent window (14) and apertures (13,15) and enter a second X-ray detector (7) for processing. The lower closed end of the cell is shown as (12). A shutter (6) is provided to seal the radioactive capsule when required.

BRIEF DESCRIPTION OF THE DRAWINGS

The invention described is referenced to the accompanying drawings as listed below.

These composite drawings of front and side elevations of the apparatus, demonstrates the relationship of the two major units, i.e., the feed sample unit providing a flow of sample into the analyzing sample unit cells situated directly below.

Figure 1:
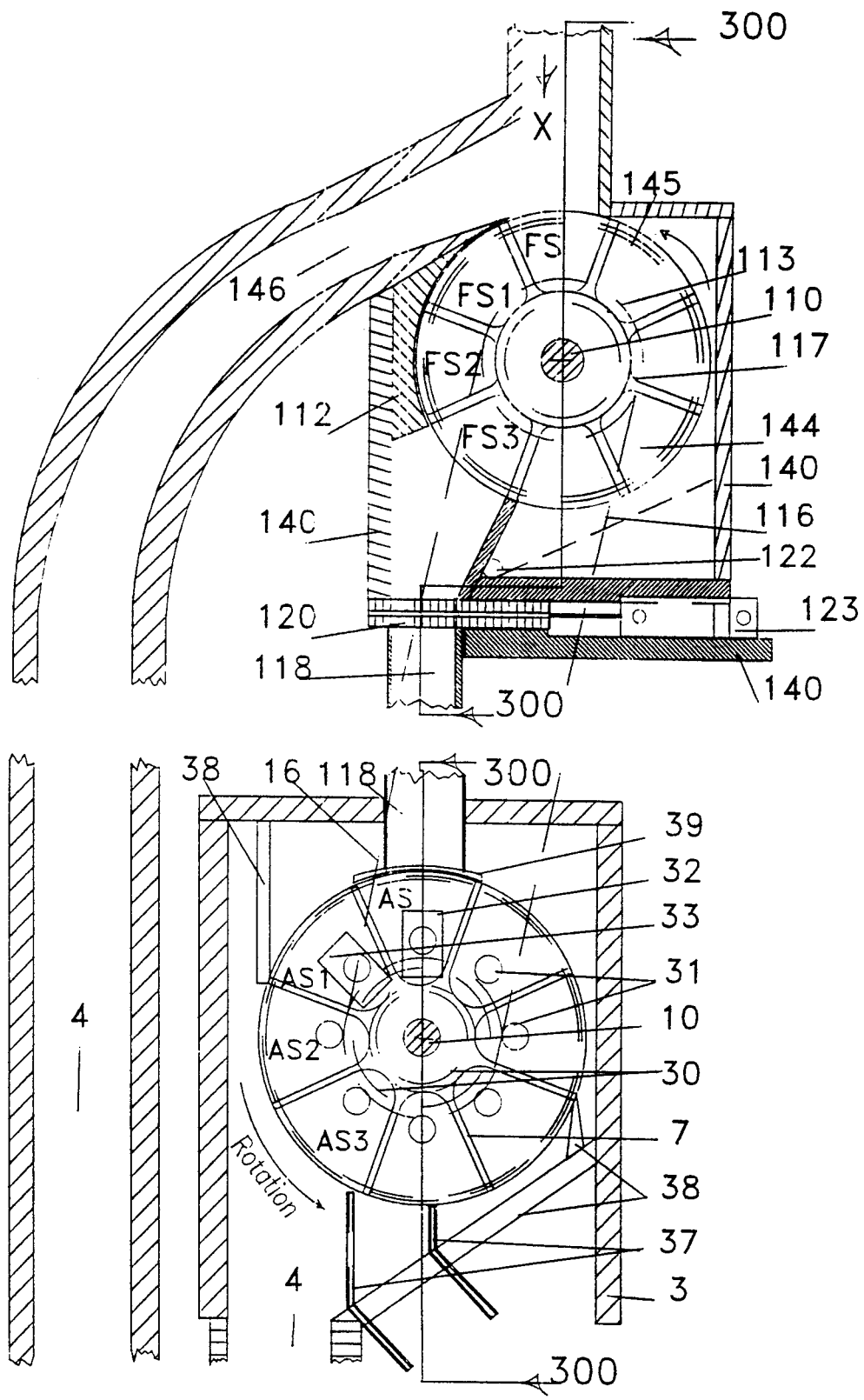
FIG. 1 is a composite drawing showing a typical assembly of cross section 300—300 (FIG. 2) of the feed sample unit, also shown in FIG. 2 and cross section 300—300 (FIG. 3) of the analyzing sample unit also shown in FIG. 3.
Figure 1A:
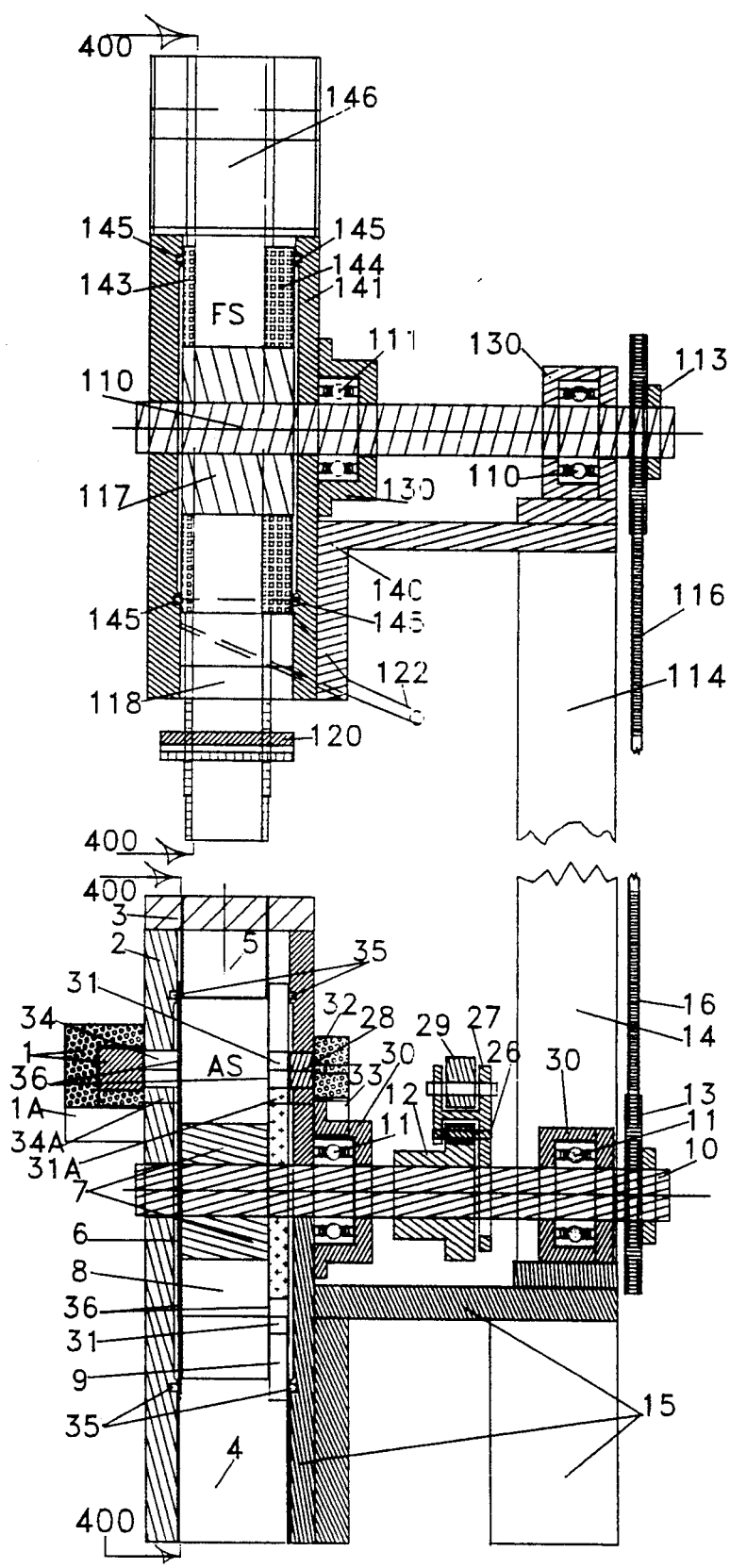
FIG. 1A is a composite drawing showing a typical assembly of cross section 400—400 (FIG. 4) of the feed sample unit also shown in FIG. 4 and a typical cross section 400—400 (FIG. 5) of the analyzing sample unit also shown in FIG. 5.
Figure 2:
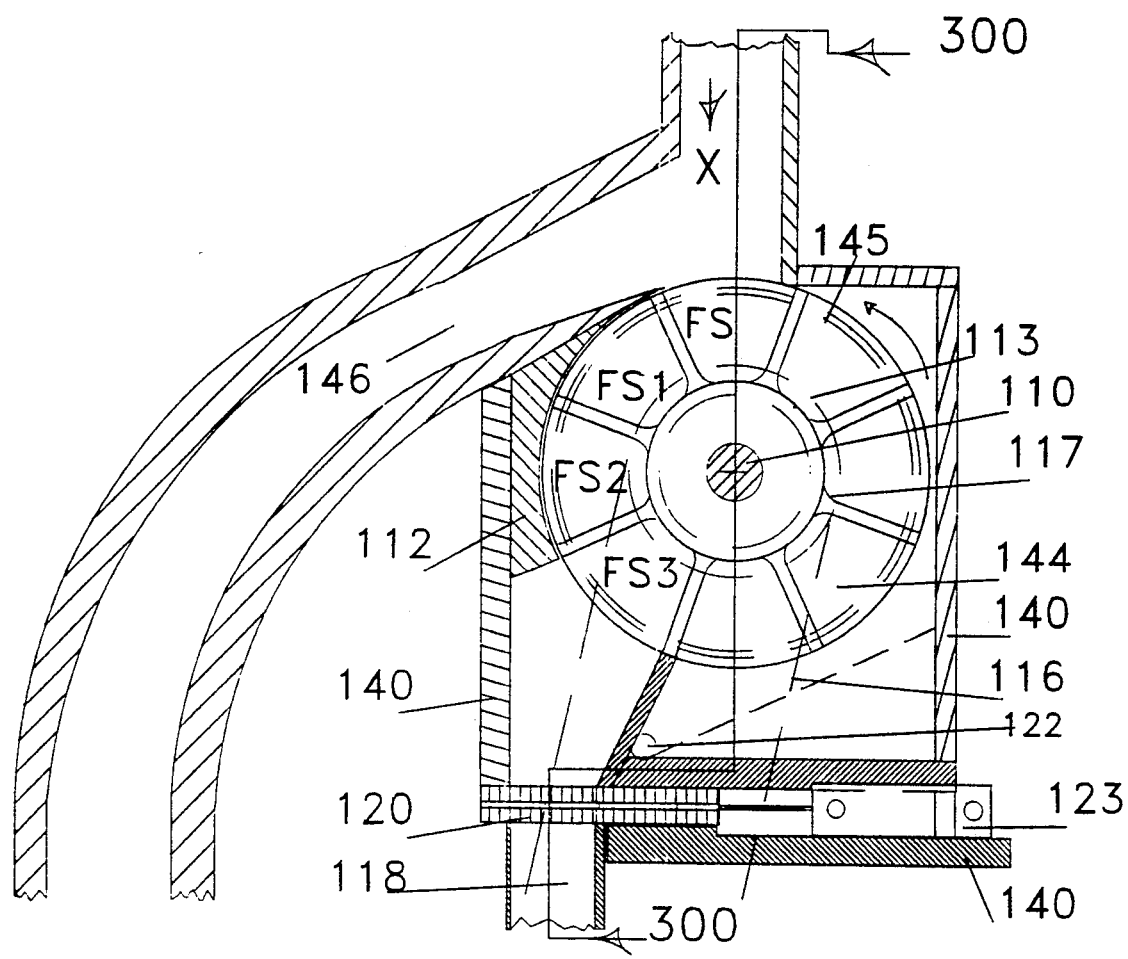

FIG. 2 is an enlarged front elevation section 300—300 of the feed sample unit, (FIG. 2.)

Figure 3:
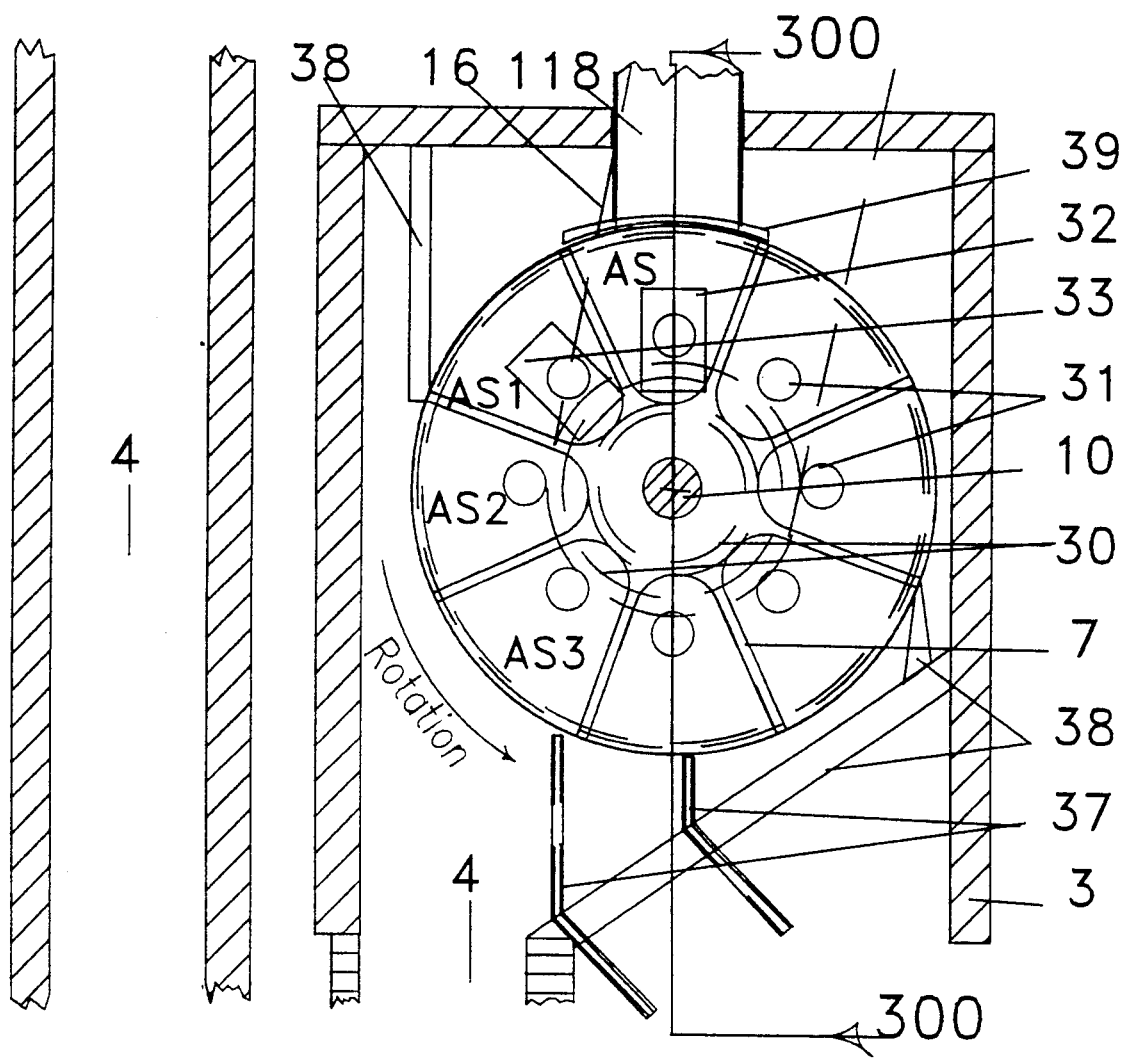

FIG. 3 is an enlarged front elevation section 300—300 of the Analyzer Sample unit, (FIG. 3.)

Figure 4:
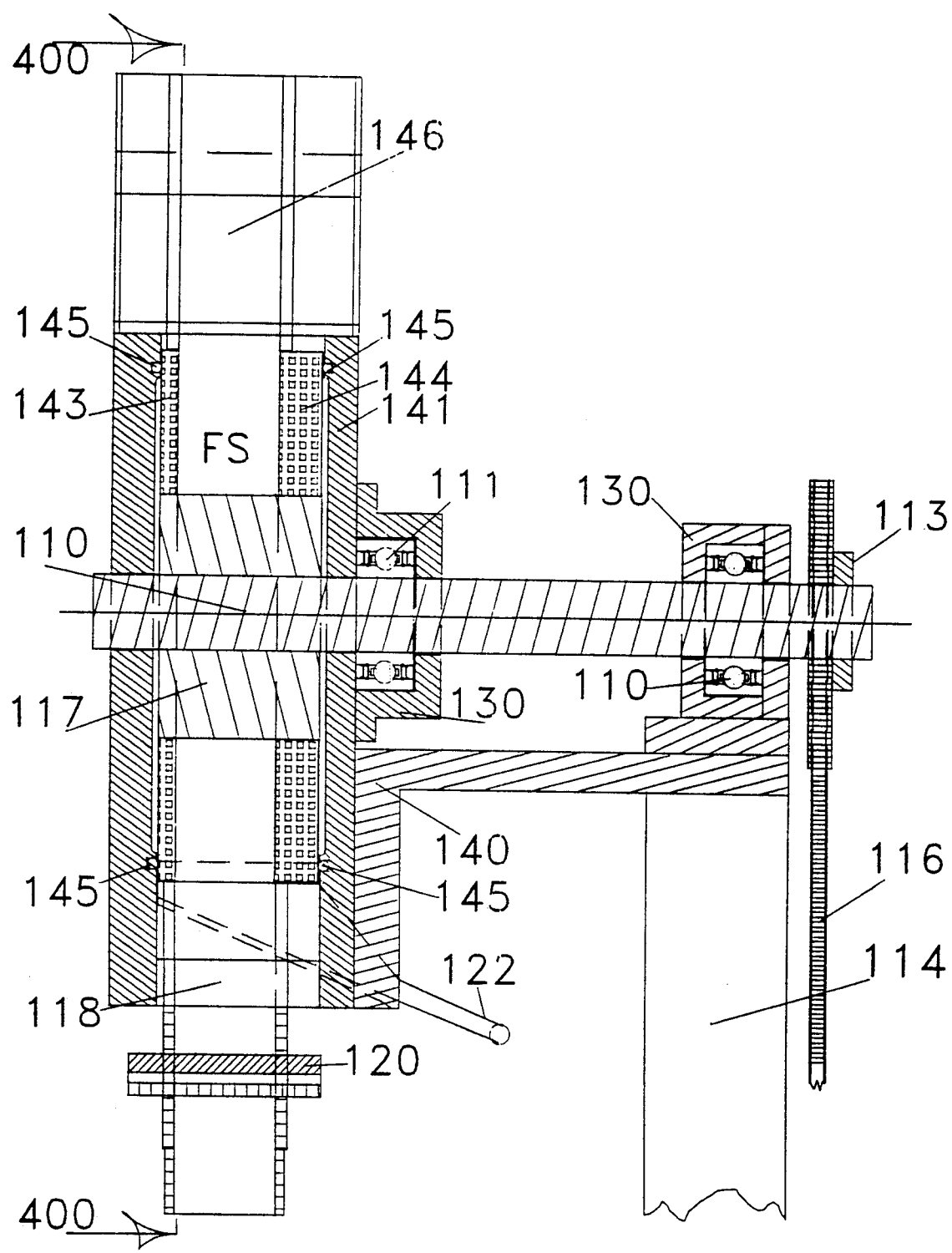

FIG. 4 is an enlarged side elevation section 400—400 of the feed sample unit, (FIG. 4.)

Figure 5:
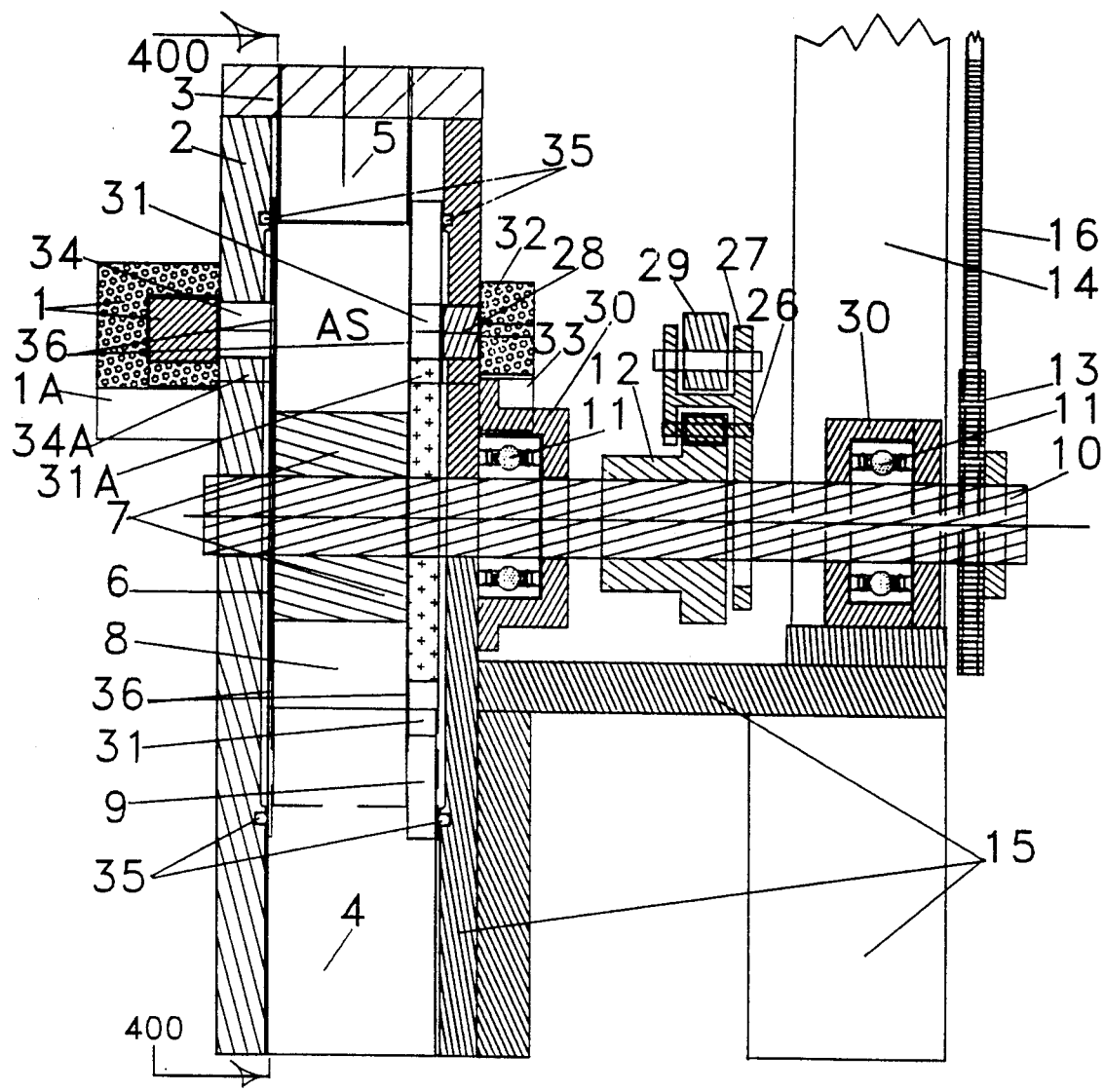

FIG. 5 is an enlarged side elevation section 400—400 of the analyzer sample unit, (FIG. 5.)

Figure 6:
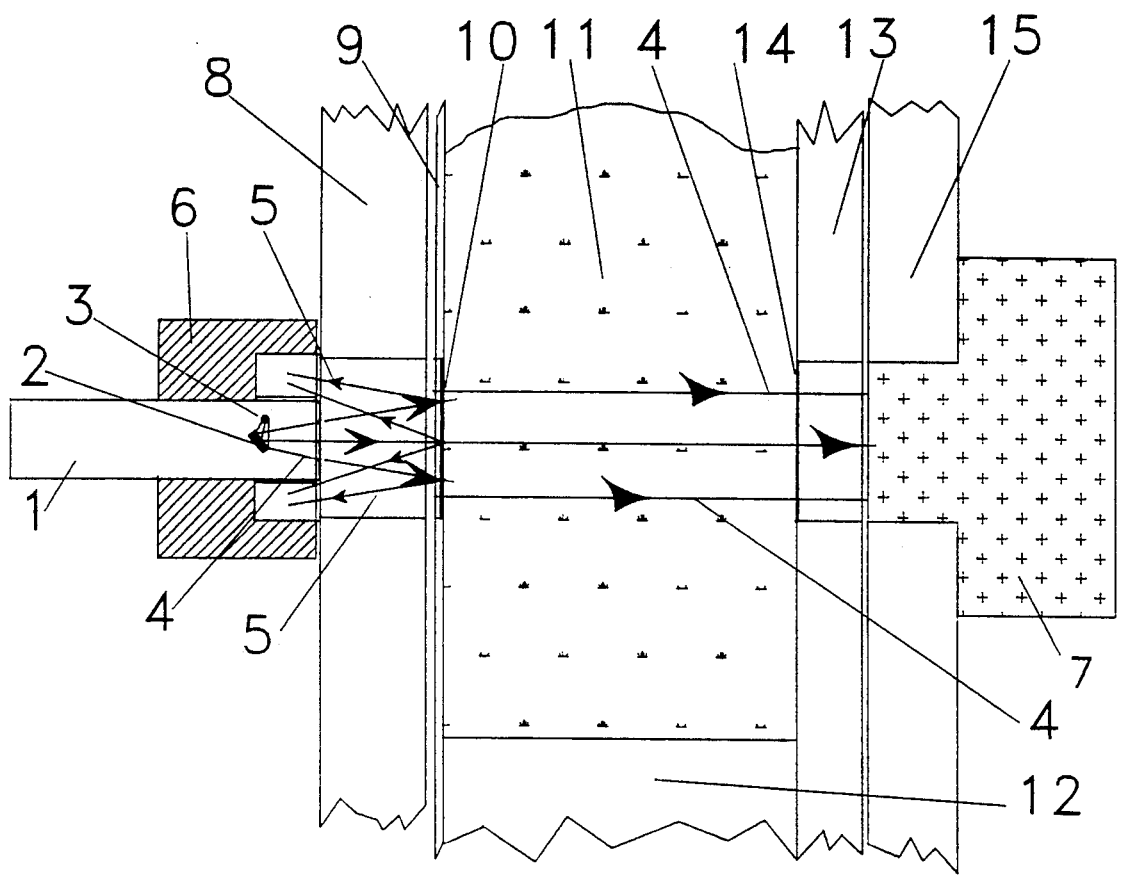

FIG. 6 is a diagram depicting a typical beam of primary X-rays passing through transparent windows to excite a sample in a cell. Secondary X-rays relating to composition of the sample are emitted from the sample, back into the front detector. Primary X-rays also penetrate the thickness of the sample and enter the rear detector.

Figure 7:
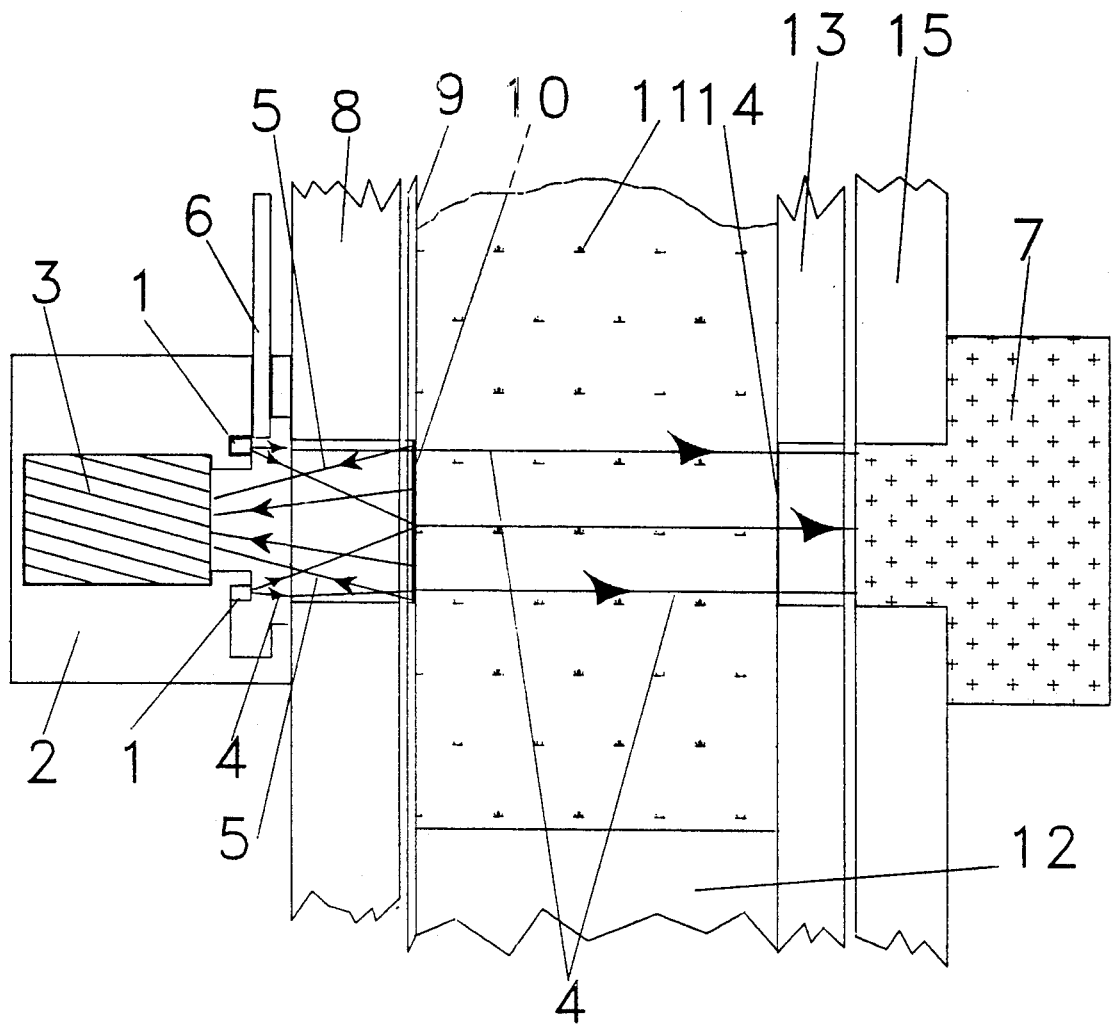

FIG. 7 is another diagram depicting X-ray paths similar to FIG. 6, and shows primary radiation from a typical radioactive-isotope source passing through transparent windows to excite a sample in a cell. The front detector receives the emitted secondary radiation relating to composition from the sample. Primary beams of energy pass through the sample thickness and enter the rear detector.

DESCRIPTION OF THE PREFERRED EMBODIMENT

In most processing plants, concentrators, beneficiators, mines etc. an assay of incoming material is essential for optimum operation. This initial assay is equally as critical as an assay of the outgoing product of final metallic concentrates or coal blended for low sulfur. A reliable timely primary assay can greatly reduce operating costs, total time needed for production, increased tonnage throughput, decreased power requirements, a decrease in the use of reagents or essential component materials required in the process.

Normal operational use of X-ray fluorescence spectroscopy in operating either X-ray tubes or radio-isotopic materials as sources of energy for X-ray fluorescence spectrometry are well known over decades of use and the employment of different types and models of X-ray detectors are also equally well known to those versed in the profession. Similarly, the use of computers and associated equipment for controlling and operating automated systems is equally well known. Therefore none of these common variables, although they will be used in this specification, will be discussed within this specification.

This invention, as previously described in the Summary of the Invention and the accompanying 8 Drawings, FIGS. 1 through 7, may use X-ray tubes having different operating characteristics and different excitation targets and in addition different radioactive isotope sources having various energy levels and characteristics, either separately or collectively mounted within the system. Particular targets for X-ray excitation and the associated detectors, and any radioactive isotope excitation unit together with its associated detector, will be selected dependent on the preferred analytical wavelength, elemental composition of the samples and type of material to be assayed. Helium gas atmosphere may also be employed when assaying certain elements or materials.

This invention provides both the desired superior elemental data outputs and an improved dry powder sample handling apparatus. This invention lies both in the method of collecting, presenting, retaining and transporting samples and also increasing the reliability and accuracy of the analytical data. A more rapid assay of the main product is also provided, thereby allowing a more realistic and rapid control of processes at lower cost.

Samples are preferably provided to the feed sample unit, in a fine ground state, of approximately 150 mesh to 350 mesh size. Coarser material may suffer a measured loss in accuracy.

Sample flows into a cell by gravity and any excess sample continues moving into the overflow exits to rejoin the product stream. Sample in the cell is retained and captured within the uppermost cell mounted within the feed sample unit. As the wheel and cell move together in the same counter-clockwise direction one cell at a time, the next cell is exposed to sample and it also fills to full level. As the wheel is caused to move every analysis period, generally variable from 30 seconds to 30 minutes or more, cells are filled consecutively and sample is continuously despatched, as commanded, to the analyzer sample unit below.

Each portion of sample, received in turn from the feed sample unit, is deposited within a cell in the analyzer sample unit and as the cells move in turn, the successive cell is filled with sample and each cell is individually assayed using an X-ray fluorescence spectrometer, through each of the windows provided, by one or more different X-ray units. The data, collected by the detectors of each X-ray unit, are related to all elements of interest within the sample, in addition to the density of sample and the packing factor of the sample in the cell. Scattered radiation at various wavelengths of interest is measured and are used as corrections for density of the sample, particle size range of the sample, inter-element corrections of elements within the sample and stability and repeatability of the X-ray system and data collecting detector electronics.

In both the feed sample unit and the analyzer sample unit, the cells are completely enclosed to prevent dust entering the atmosphere and also to return excess and discarded sample back to the downstream side of the product.

The invention produces an assay relating to the elemental composition of a material that is substantially proportional to the concentration of that element, corrected for inter-element effects, density, packing factor, etc.

If any cell does not contain sufficient sample for analysis a detection system will operate and alert the operator.

Calibration of all elements within a composition is achieved by using either powdered samples of known composition or manufacture or by inserting solid samples of known composition into one or more of the sample cells. One or more solid samples may be installed permanently in any one of the cells in the analyzer unit to provide a consistent test of the unit's and the operating system's stability and performance.

It will be understood, of course, that the invention may be practiced in ways other than described herein, and that the invention is not limited to the particular implementation or example described. More particularly it will be understood that the invention may be of variable dimensions and may be proportioned to fit a particular large or small application and that where an X-ray fluorescence tube or source is mentioned, said X-ray tube or radioactive Isotope excitation source may be of different designs and supplied with variable power supplies and dimensions. Also the detectors may be of many varieties ranging, for e.g., from proportional detectors to solid state counters operating in either a digital or analog mode.

Methods of controlling the total system are variable depending on particular processes or on-line applications. The feed and analyzer units may be driven independently by mechanical, hydraulic or electrical devices or in a combined mode using sprockets and chains or gears, or from any electrical or electronic power source available for the application and said units may be separated by any reasonable distance.

It is preferred that the feed and analyzer units be supervised by computer control or logic control system and the output data be computed by a computer program that provides a rapid and reliable means of operation.

The invention claimed is:

1. An apparatus for collecting, retaining, transporting and analyzing by X-ray fluorescence spectroscopy means a flow of dry powder samples:
   comprising a mechanical system, called a feed sample, having a number of cells, each said cell comprises one closed end, four walls and one open end, two parallel walls of said cells are of plates of circular continuous sections, the open end of each cell permits the acceptance and discharge of dry powder samples each said cell is moved sequentially into a vertical loading position and is automatically filled with a sample of a dry product stream, said sample being a flowing portion of a main process stream, said cell containing said sample moves counter-clockwise after filling and the following empty cell occupies the loading position, said continuous flowing process sample stream fills each cell in turn and said samples are temporarily restrained within each said cell in motion by means of a sample retention plate covering the open peripheral end as each said cell in turn progressively rotates and dispenses said sample, said sample exits the feed sample unit, by gravity, standard means are used to provide motion to move said cells consecutively through sample loading position, sample retention positions and sample dispensing position, where said sample is sequentially deposited into a unit to be assayed by a mechanical means similar to the feed sample unit having similar shaped cells, being one of a number of cells composed of one closed end, four walls and one opened as in the feed sample unit, having in addition, two X-ray transparent windows positioned in each cell in each of one pair of plates of circular continuous section forming parallel walls of each cell, said cell windows in each cell being in optical alignment to each other and transparent to X-ray spectroscopic energy levels, said cells comprise the analyzer sample unit, wherein said retained samples in said analyzer cells are presented for analysis by being sequentially moved into a first analysis position and samples analyzed through said transparent windows by X-ray fluorescence means, using an attached first X-ray tube analyzer and associated elemental detectors and associated density and intensity detectors, mounted over one pair of the available X-ray transparent window areas, to analyze said samples for a number of elements ranging from Na to U and intensity data relating to particle size, density and compacting factors, said X-ray tube having standard X-ray tube targets including W, Cr, Cu, Mo, Pt, Ag, Rh and associated detectors are selected to accept X-ray primary and secondary beam energy levels emanating from said sample, said means and techniques of X-ray fluorescence spectroscopic analysis to be used in the analyzing positions provided for analysis by X-ray spectroscopy, and where said apparatus is manufactured to a size commensurate with analyzing variable quantities of said samples within a given period and where the dimension and number of cells is variable, and where said apparatus and number of said cells, may be manufactured in a size commensurate where said samples may be inserted manually and sequentially into said feed sample unit as in a manual laboratory mode, and said samples analyzed in an automated mode in the analyzer sample unit, and said apparatus whereby feed sample cell and analyzer cell motions, operation and sequential rotation of the apparatus are controlled and programmed by a microprocessor means, and said apparatus, whereas data from spectroscopic elemental detectors and associated density and intensity data detectors and cell movement data are collected, evaluated, processed and data output are produced by microprocessor means, and said apparatus, whereby apparatus is added for inserting an atmosphere of helium gas means into areas of analyzer sample cells to analyze elements ranging from Na to S within said samples and said cells, and said apparatus, where said X-ray transparent windows in each analyzer sample unit are of thickness from 0.005 mm to 20 mm, and are of standard materials, and said apparatus of claims listed above, where said motions of said feed sample and analyzer sample cells may be a linear function.

2. The apparatus of claim 1, whereas analysis of said samples is achieved using radioactive isotope X-ray fluorescence spectroscopic source means and associated elemental detectors and associated density and intensity detectors.

3. The apparatus of claim 2 whereas a plurality of said different excitation source means and associated elemental detectors and associated density and intensity detectors, are combined in places designated for analysis.

* * * * *